(12) United States Patent
Liu

(10) Patent No.: US 10,136,915 B2
(45) Date of Patent: Nov. 27, 2018

(54) ULTRASOUND NEEDLE GUIDE APPARATUS

(71) Applicant: LOVING HEART MEDICAL TECHNOLOGY INC., Monterey Park, CA (US)

(72) Inventor: Ming-Wei Liu, Monterey Park, CA (US)

(73) Assignee: LOVING HEART MEDICAL TECHNOLOGY INC., Monterey Park, CA (US)

( * ) Notice: Subject to any disclaimer, the term of this patent is extended or adjusted under 35 U.S.C. 154(b) by 679 days.

(21) Appl. No.: 14/605,673

(22) Filed: Jan. 26, 2015

(65) Prior Publication Data

US 2016/0213398 A1 Jul. 28, 2016

(51) Int. Cl.
*A61B 8/14* (2006.01)
*A61B 17/34* (2006.01)
*A61B 8/08* (2006.01)
*A61B 8/00* (2006.01)

(52) U.S. Cl.
CPC .......... *A61B 17/3403* (2013.01); *A61B 8/085* (2013.01); *A61B 8/0841* (2013.01); *A61B 8/0891* (2013.01); *A61B 8/462* (2013.01); *A61B 8/4455* (2013.01); *A61B 2017/3413* (2013.01)

(58) Field of Classification Search
None
See application file for complete search history.

(56) References Cited

U.S. PATENT DOCUMENTS

| 5,758,650 A * | 6/1998 | Miller ................ A61B 17/3403 600/461 |
| 5,924,992 A | 7/1999 | Park et al. |
| 2007/0073155 A1* | 3/2007 | Park ..................... A61B 8/0833 600/461 |
| 2010/0160787 A1* | 6/2010 | Gorzitze .............. A61B 8/0833 600/461 |
| 2011/0166451 A1* | 7/2011 | Blaivas ................ A61B 17/282 600/439 |
| 2013/0237811 A1* | 9/2013 | Mihailescu ............ A61B 5/064 600/424 |

* cited by examiner

*Primary Examiner* — Joel F Brutus
(74) *Attorney, Agent, or Firm* — Muncy, Geissler, Olds & Lowe, P.C.

(57) ABSTRACT

An ultrasound needle guide apparatus to aid guidance of a puncturing needle to locate blood vessel positions of a living body and perform puncturing operation includes an ultrasound detection device, a display element connected to the ultrasound detection device in a rotatable manner and a needle positioning aid element fastened to the ultrasound detection device. The display element obtains ultrasonic signals from the ultrasound detection device and displays the blood vessel positions of the living body in an image fashion. The ultrasound needle guide apparatus is directly in contact with the intended ultrasound probing position so that users can directly and intuitively observe the blood vessel position through the display element, and swivel the display element according to operating position to control adjustment of display angle, and perform blood vessel puncturing operation via the needle positioning aid element to meet use requirement.

9 Claims, 6 Drawing Sheets

ULTRASOUND NEEDLE GUIDE APPARATUS

FIELD OF THE INVENTION

The present invention relates to an ultrasound apparatus and particularly to an ultrasound needle guide apparatus.

BACKGROUND OF THE INVENTION

Puncturing blood vessels is a common practice in medical treatment of human body. Medical personnel have to learn through training and experience to acquire an accurate technique of performing vascular puncturing. However, the blood vessels of patients are not always easily discernible. Especially for elderly patients, the blood vessel becomes calcified, thickened and lost elasticity which makes puncturing the blood vessels more difficult.

Aside from puncturing superficial blood vessels, performing puncture of blood vessel at a deeper location may become particularly challenging. In such a situation, ultrasound image may become very useful and important to guide the direction and depth of the needle to perform a successful and accurate puncturing of a blood vessel without conventional repeated trial-and-error method.

For instance, U.S. Pat. No. 5,924,992 entitled "Semi-compliant needle guide for use with ultrasound transducers" discloses a probe to generate and receive ultrasonic waves that is in contact with a body position where blood vessel puncturing is intended to perform ultrasound detection. Though an external screen connected to the probe ultrasound images can be seen to facilitate blood vessel puncturing operation. However, the operator has to look at the external screen during the blood vessel puncturing operation rather than directly looking at the human body where the puncturing operation is being performed. This design is seriously deficient of human intuition and working ergonomics which are extremely importantly for any procedure tool. The operator has to control the ultrasound needle guide with one hand and control the needle to perform blood vessel puncturing operation with the other hand while the eyes have to look at the external screen. Thus, the design makes the procedure cumbersome and is prone to cause inaccurate puncturing a number of times before making a correct one.

Furthermore, as the blood vessel generally is very small in diameter, a slight deviation could make the needle skewed from the correct puncturing position that could affect the later treatment or surgical operation. Moreover, the aforesaid prior art, referring to its FIGS. 1 and 2, provides a closed type needle locating and guiding bore to facilitate needle positioning and blood vessel puncturing. After the puncturing operation is finished, normally, a guide wire is needed to be inserted into the lumen of the puncturing needle and then advance into the lumen of blood vessel while maintaining the position of the needle tip in the lumen of blood vessel. With the closed type bore being in conjunction with the needle, the ultrasound transducer cannot be removed while performing inserting a guide wire into the blood vessel. This demand of action adds more technical difficulty and increase the chance of failure due to the fact that maintaining a needle tip in the small luminal space of blood vessel is a very delicate move.

SUMMARY OF THE INVENTION

The primary object of the present invention is to solve the problems of inconvenience working position and deficiency in accuracy from current conventional method of ultrasound needle guidance.

To achieve the foregoing object, the present invention focus on working ergonomics and puncturing accuracy when using an ultrasound needle guide apparatus. The ultrasound needle guide apparatus includes an ultrasound detection device, a display element connected to the ultrasound detection device in a rotatable manner and a needle positioning aid element fastened to the ultrasound detection device. The ultrasound detection device includes a probe head in contact with the blood vessel positions of the living body to make detection via ultrasonic waves, a grip shell connected to the probe head, a first hinge portion located on the grip shell, and an image process unit located in the grip shell and electrically connected to the probe head. The display element includes a second hinge portion hinged on the first hinge portion and a display screen electrically connected to the image process unit. The display screen forms the electric connection with the image process unit through the first hinge portion and the second hinge portion to obtain ultrasonic signals from the probe head and display the blood vessel positions of the living body. The needle positioning aid element is fixedly located on the ultrasound detection device and abutting the probe head to aid positioning of the puncturing needle and performing the puncture operation on the vessel positions of the living body. Through the construction set forth above, the invention provides many advantageous features, notably:

1. The display element is directly mounted onto the ultrasound detection device to allow the operator to move intuitively the probe head according to ultrasound images, hence can quickly and accurately locate the blood vessel locations.

2. The display screen of the display element can be adjusted according to the visual angle of the operator to optimize the working ergonomics.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
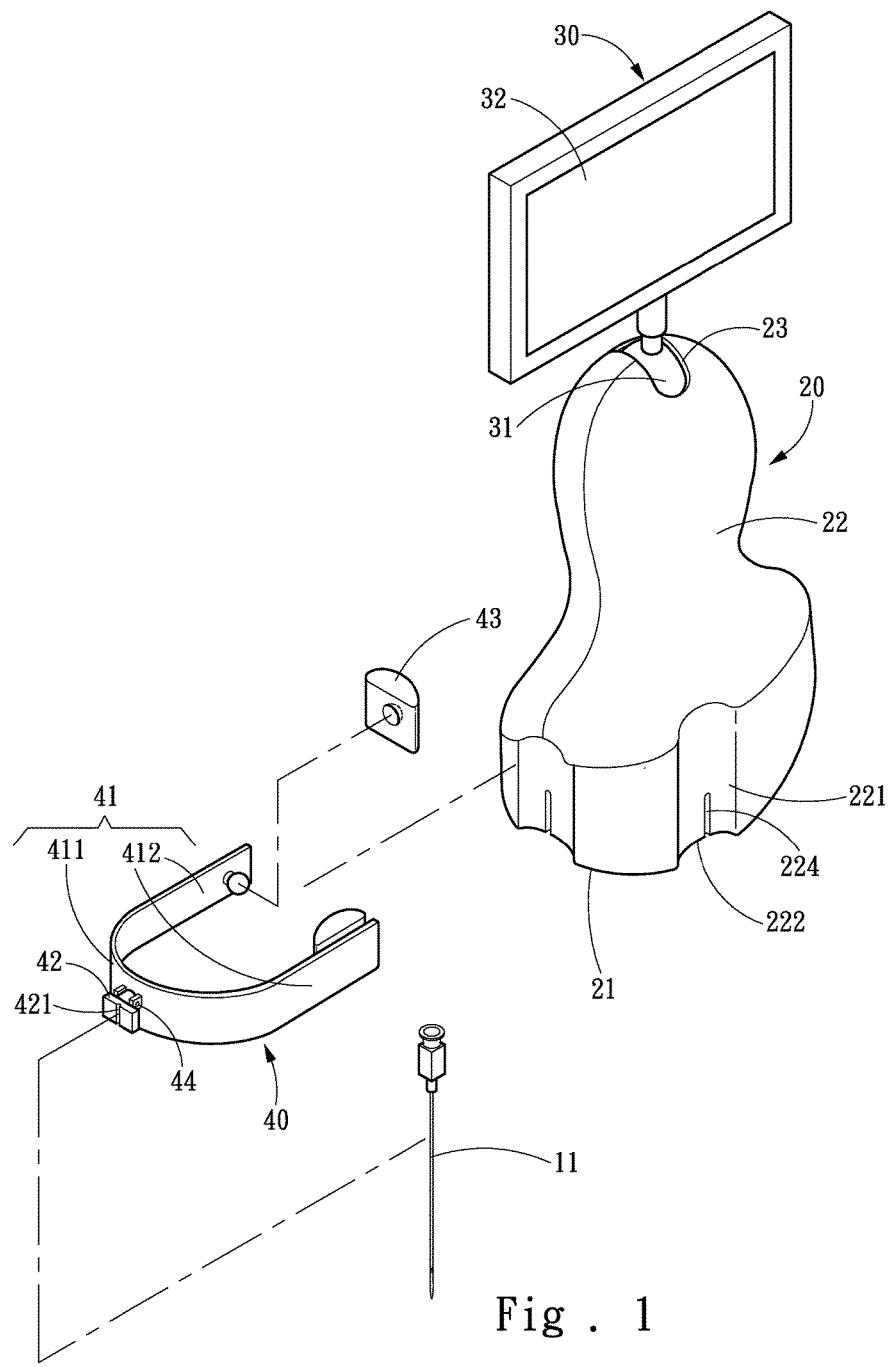
FIG. 1 is a schematic perspective view of an embodiment of the invention.
Figure 2:
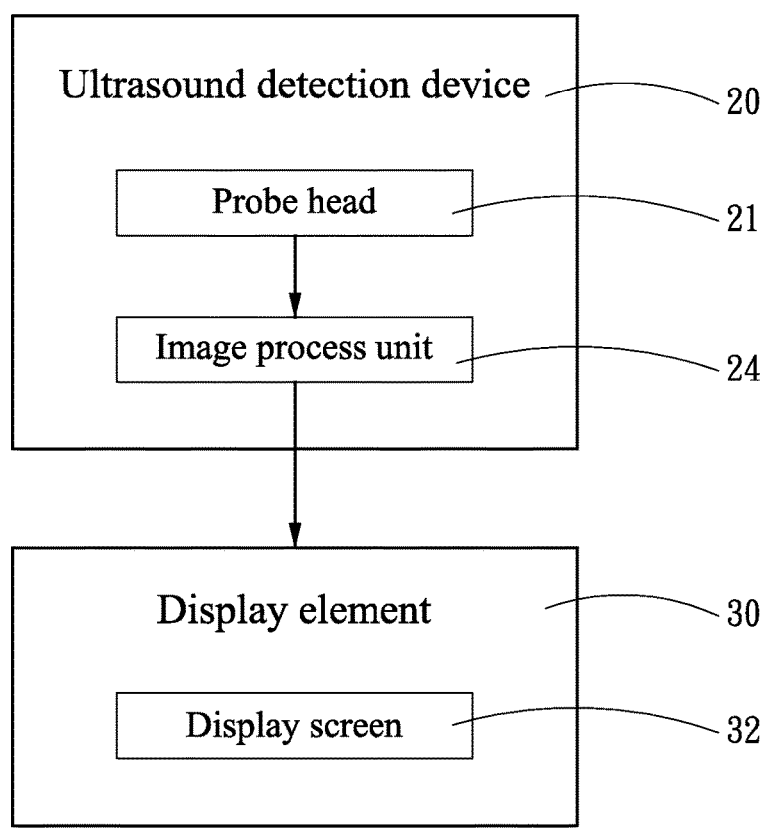
FIG. 2 is a unit block diagram of an embodiment of the invention.
Figure 4A:
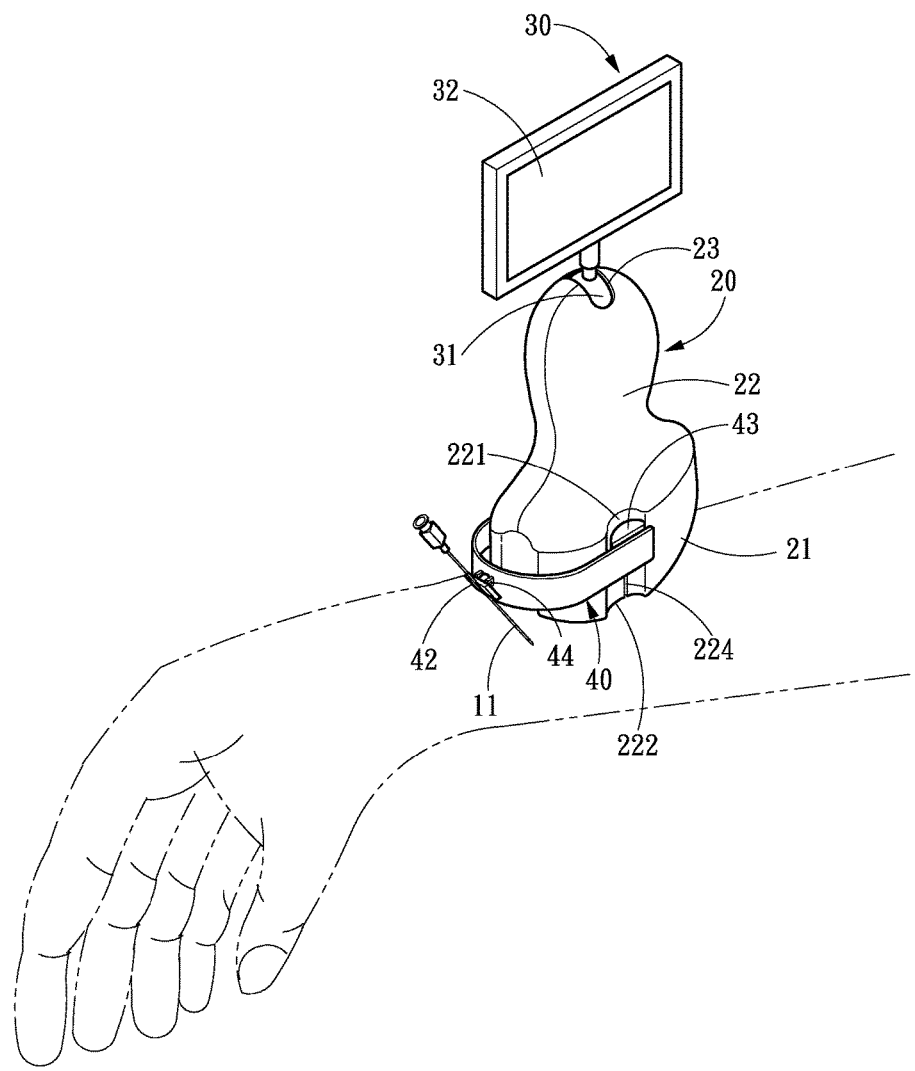
FIGS. 4A and 4B are schematic views of an embodiment of the invention in use conditions.

Please referring to FIGS. 1, 2 and 4A, the present invention aims to provide an ultrasound needle guide apparatus to aid guidance of a puncturing needle 11 to locate blood vessel positions of a living body 12 and perform puncturing operation. It includes an ultrasound detection device 20, a display element 30 connected to the ultrasound detection device 20 in a rotatable manner and a needle positioning aid element 40 fastened to the ultrasound detection device 20. The ultrasound detection device 20 includes a probe head 21 in contact with the blood vessel positions of the living body 12 to perform detection thereof via ultrasonic waves, a grip shell 22 connected to the probe head 21, a first hinge portion 23 located on the grip shell 22, and an image process unit 24 located in the grip shell 22 and electrically connected to the probe head 21. A user can grip and move the grip shell 22 to slide the probe head 21 on an intended position of the living body 12 to get ultrasonic signals through conversion of the probe head 21 and the image process unit 24. The display element 30 includes a second hinge portion 31 hinged on the first hinge portion 23 and a display screen 32 electrically connected to the image process unit 24. The display screen 32 forms electric connection with the image process unit 24 through the first hinge portion 23 and the second hinge portion 31 to get the ultrasonic signals from the probe head 21 and display the blood vessel positions of the living body 12. The needle positioning aid element 40 can be fixedly located on the ultrasound detection device 20 and abutting the probe head 21. In this embodiment the needle positioning aid element 40 includes a body 41 fixed on the ultrasound detection device 20 and a positioning aid support portion 42 at one side of the body 41 remote from the ultrasound detection device 20. The positioning aid support portion 42 includes a first positioning trench 421 matching the diameter of the puncturing needle 11 to hold and anchor thereof to aid positioning and perform puncturing operation on the blood vessel positions of the living body 12.

In this embodiment the second hinge portion 31 is a protruding sphere, and the first hinge portion 23 is an arched groove against the second hinge portion 31, therefore the display element 30 can be adjusted its angle relative to the grip shell 22 via the first hinge portion 23 as an axis to change the display direction. On the other hand, the spherical structure and arched groove of the first hinge portion 23 and the second hinge portion 31 also can be switched according to design requirement or the like.

Figure 3:
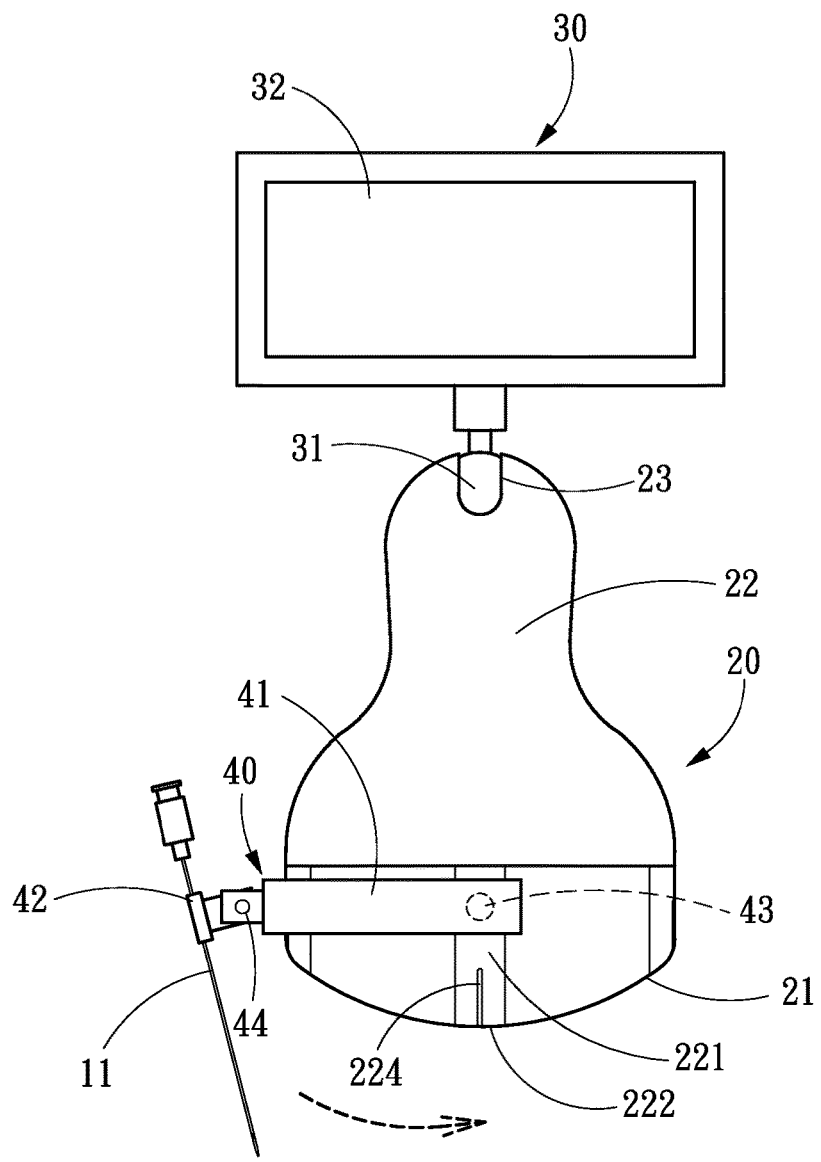
FIG. 3 is a schematic view of an embodiment of the invention showing a puncturing angle adjustment condition.

Please also referring to FIG. 3, in practice, the body 41 of the needle positioning aid element 40 includes a curved section 411 and two clamp sections 412 at two ends of the curved section 411. The two clamp sections 412 collaborate with the curved section 411 to clamp the grip shell 22 from two sides of the grip shell 22. In other words, the body 41 is formed in a U shape to hold the curved section 411. The needle positioning aid element 40 further has two pivotal positioning members 43 hinged on two abutting sides of the two clamp sections 412 so that the two clamp sections 412 can clamp securely the grip shell 22, thereby the needle positioning aid element 40 can be swiveled about the pivotal positioning members 43 as an axis to adjust the puncturing angle of the puncturing needle 11 held on the positioning aid support portion 42 against the living body 12. Due to different depths of blood vessels, the needle positioning aid element 40 needs angular adjustment to control the angle of the puncturing needle 11 to adjust the puncturing angle and depth. Furthermore, the angle of the positioning aid support portion 42 against the curved section 411 can also be adjusted via an angle adjustment member 44 hinged on the curved section 411, thereby to control the puncturing angle of the puncturing needle 11.

In addition, the grip shell 22 has two guide troughs 221 respectively corresponding to the two clamp sections 412 with an axis perpendicular to the probe head 21. The guide trough 221 has an opening 222 at one end abutting the probe head 21 to allow the needle positioning aid element 40 to move along the guide trough 221 toward the probe head 21 outside the grip shell 22 to be released from the clamp and anchor state. Hence, when the needle positioning aid element 40 is connected to the ultrasound detection device 20, it can be moved horizontally on the surface of the living body 12 to locate the blood vessel positions. Since the needle positioning aid element 40 and the ultrasound detection device 20 are moved vertically along the guide troughs 221 via the clamp sections 412, they can be connected steadily. On the other hand, the guide troughs 221 can be clamped merely from two sides without limited to other specific directions. Moreover, each guide trough 221 further can include a second positioning trench 224 matching the diameter of the puncturing needle 11 to be leaned thereof for positioning. Hence, even if the needle positioning aid element 40 is not in use the second positioning trench 224 can aid positioning of the puncturing needle 11 to puncture the blood vessel positions of the living body 12.

It is to be noted that, in this embodiment the second positioning trench 224 is located in the guide trough 221. In the event that the design aims to have no needle positioning aid element 40, then the second positioning trench 224 can be directly located on the grip shell 22 abutting the probe head 21 to directly aid positioning of the puncturing needle 11.

Please refer to FIG. 4A for the invention in use conditions as follows: Generally speaking, performing needle puncture using ultrasound guidance require a sterile environment, thus the ultrasound detection device 20 is wrapped via a transparent plastic pouch (not shown in the drawing) to isolate the probe head 21 from in direct contact with the living body 12; next, couple the needle positioning aid element 40 and the ultrasound detection device 20 together, and slide them on the skin over the intended blood vessel. During this process the display element 30 can directly display images detected by the probe head 21 to allow the user to directly and intuitively judge the blood vessel position. Then the puncturing needle 11 can be positioned via the aid of the needle positioning aid element 40 to perform blood vessel puncturing operation while the user is directly looking at the blood vessel image, thereby can improve operation precision and reliability.

Figure 4B:
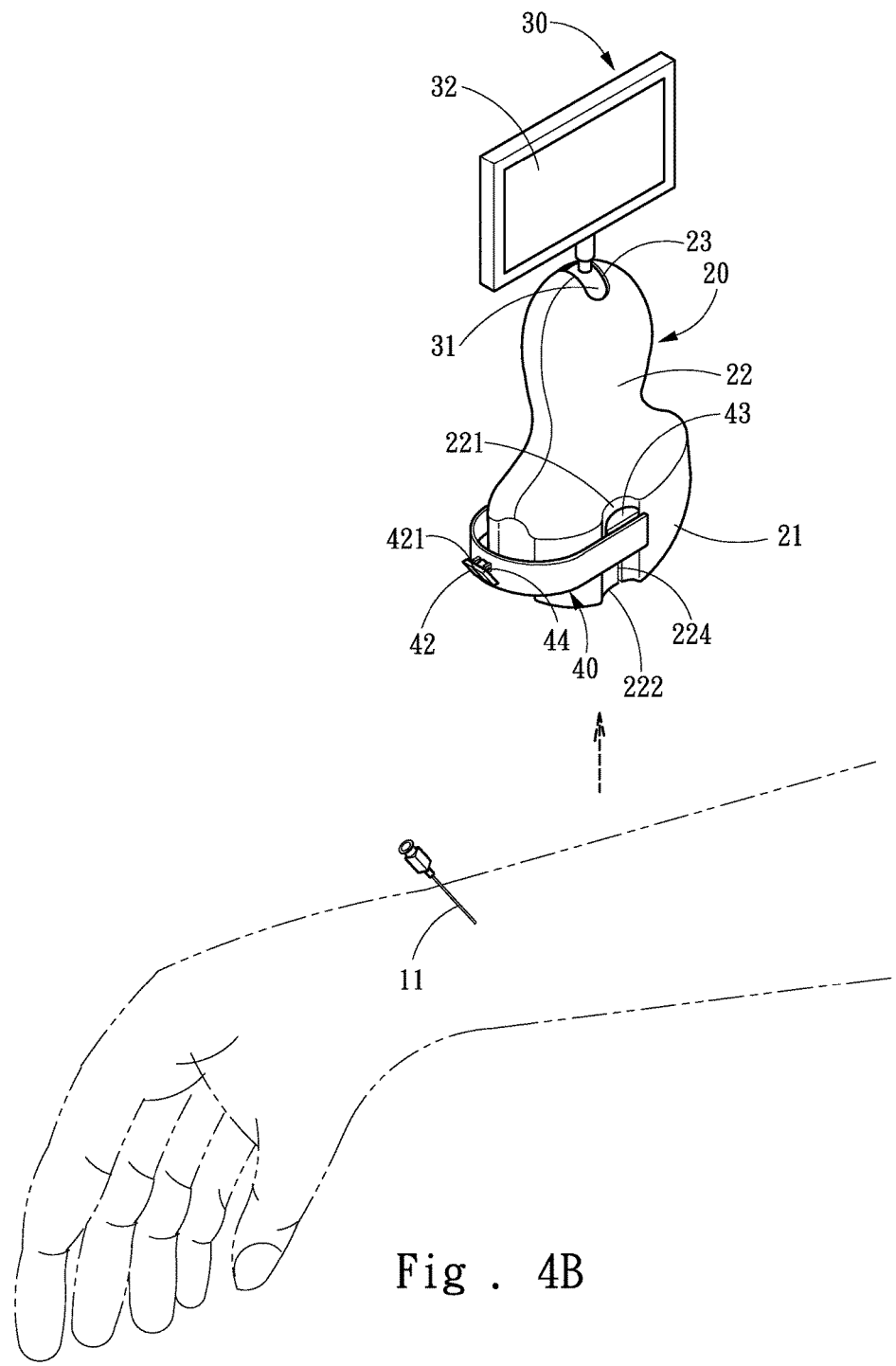

After the blood vessel puncturing operation is finished, please referring to FIG. 4B, the ultrasound detection device 20 and the needle aid positioning element 40 can be removed directly from the puncturing needle 11 via the first positioning trench 421. The entire process is neat and straightforward, and can meet user's working ergonomics. Once the puncturing needle 11 is positioned, the downstream blood vessel puncturing operation can be performed as desired.

Figure 5:
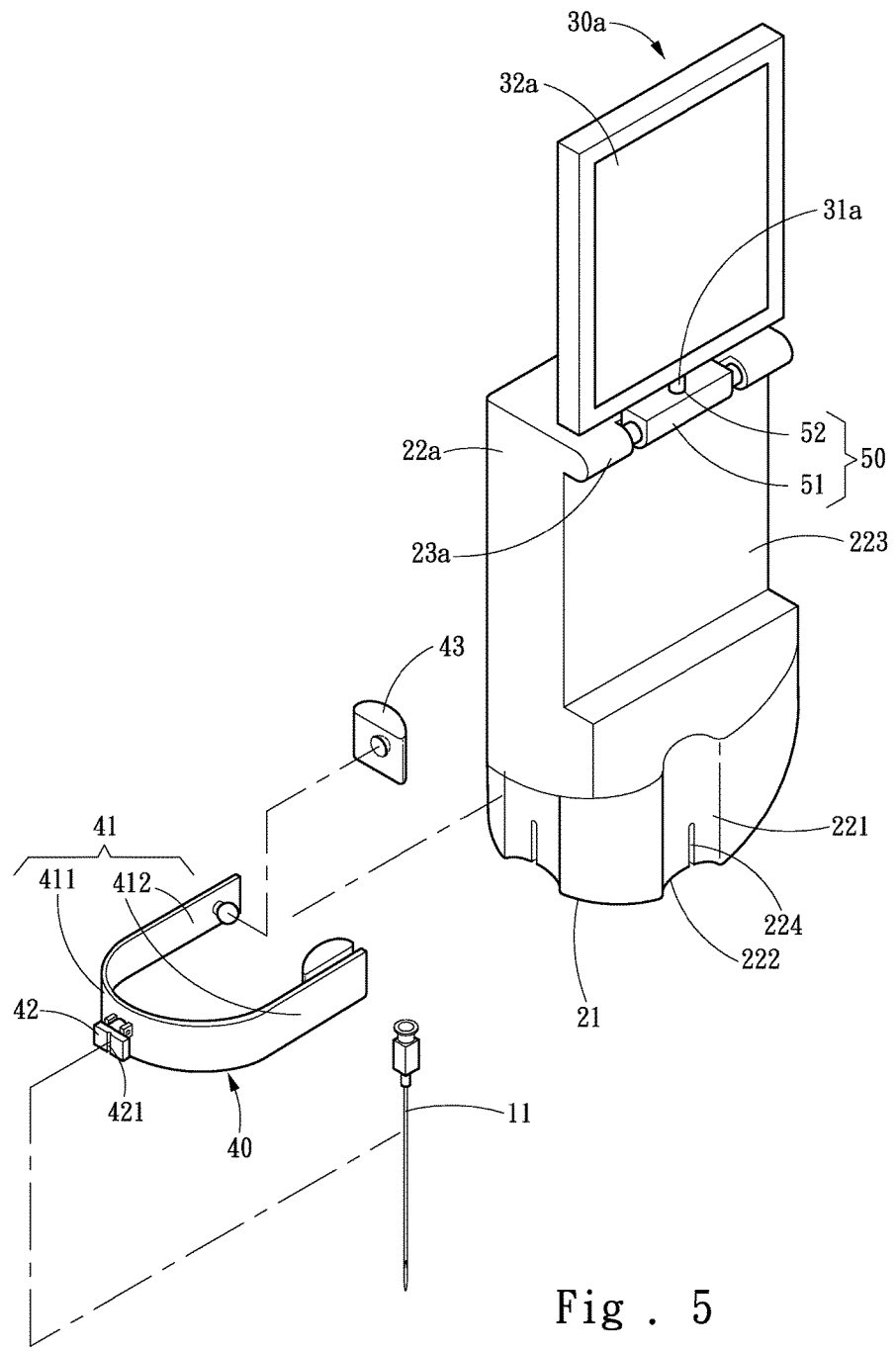
FIG. 5 is a schematic view of another embodiment of the invention to be assembled for use.

Aside from the angle adjustment between the display element 30 and the grip shell 22 that is performed via a sphere collaborating with a groove as previously discussed, the invention further provides another embodiment as shown in FIG. 5 in which the grip shell 22a and the display element 30a are bridged by a connector 50. The connector 50 includes a first connector 51 hinged on the first hinge portion 23a and a second connector 52 hinged on the second hinge portion 31a. The first hinge portion 23a and the first connector 51 have a swivel axis perpendicular to the swivel axis of the second hinge portion 31a and the second connector 52. The grip shell 22a further has a holding recess 223 corresponding to the display element 30a for holding thereof. When not in use the display element 30a can be held inside to save space. When in use the display element 30a can be flipped outside the holding recess 223 via the connector 50, and the display angle of the display screen 32a can be adjusted as desired to meet user's requirement.

As a conclusion, the invention can provide features as follows:

1. The display element is directly mounted onto the ultrasound detection device to allow the operator to move intuitively the probe head according to the ultrasound image, hence can quickly and accurately locate the blood vessel positions.

2. The display screen of the display element can be adjusted according to the operator's visual angle without moving physically to the display position of display screen, therefore can better meet use requirement.

3. Through the design of the connector and the holding recess storing and increased using space of the entire apparatus, hence the usability improves.

4. Through the design of the curved section and the clamp sections of the body, collaborated with the guide trench of the grip shell, the needle positioning aid element can be moved steadily horizontally with the movement of the grip shell. Through the vertical movement thereof the needle positioning aid element and the grip shell can be separated easily to meet use requirement.

5. Through the pivotal positioning member the puncturing angle of the puncturing needle relative to the living body can be adjusted to facilitate adjustment of the puncturing depth.

What is claimed is:

1. An ultrasound needle guide apparatus to aid guidance of a puncturing needle to locate blood vessel positions of a living body and perform puncturing operation, comprising:
   an ultrasound detection device including a probe head which is configured to contact with the living body to detect the blood vessel positions via ultrasonic waves, a grip shell connected to the probe head, a first hinge portion located on the grip shell, and an image process unit located in the grip shell and electrically connected to the probe head;
   a display element which is rotatably connected to the grip shell and includes a second hinge portion hinged on the first hinge portion and a display screen electrically connected to the image process unit through the first hinge portion and the second hinge portion to get ultrasonic signals from the probe head and display the blood vessel positions of the living body; and
   a needle positioning aid element fastened to the ultrasound detection device and located beside the probe head, including a body fixed on the ultrasound detection device and a positioning aid support portion located at one side of the body remote from the ultrasound detection device to aid positioning of the puncturing needle;
   wherein the body includes a curved section and two clamp sections at two ends of the curved section, the two clamp sections is corresponding with the curved section to clamp the grip shell from two sides of the grip shell, the grip shell includes two guide trough respectively corresponding to the two clamp sections that has an axis perpendicular to the probe head.

2. The ultrasound needle guide apparatus of claim 1, wherein the second hinge portion is a protruding sphere, the first hinge portion being an arched groove against the second hinge portion, the display element and the grip shell forming an included angle there between that is adjustable via the first hinge portion as an axis to adjust display direction of the display element.

3. The ultrasound needle guide apparatus of claim 1 further including a connector to bridge the grip shell and the display element, the connector including a first connector hinged on the first hinge portion and a second connector hinged on the second hinge portion, the first hinge portion and the first connector forming a first swivel axis perpendicular to a second swivel axis formed between the second hinge portion and the second connector.

4. The ultrasound needle guide apparatus of claim 1, wherein the positioning aid support portion includes a first positioning trench matching the diameter of the puncturing needle to hold and anchor the puncturing needle.

5. The ultrasound needle guide apparatus of claim 1, the needle positioning aid element further including two pivotal positioning members hinged on two abutting sides of the two clamp sections to allow the two clamp sections to clamp the grip shell and anchor thereon such that the needle positioning aid element is capable of swivel with the pivotal positioning members as an axis to adjust the puncturing angle of the puncturing needle held on the positioning aid support portion relative to the living body.

6. The ultrasound needle guide apparatus of claim 5, wherein the guide trough including an opening at one end abutting the probe head.

7. The ultrasound needle guide apparatus of claim 6, wherein the guide trough includes a second positioning trench matching the diameter of the puncturing needle to hold and anchor the puncturing needle.

8. The ultrasound needle guide apparatus of claim 1, wherein the needle positioning aid element further includes a pivotal positioning member hinged on the body and the positioning aid support portion.

9. The ultrasound needle guide apparatus of claim 1 further including a second positioning trench located on the grip shell abutting the probe head and matching the diameter of the puncturing needle to hold and anchor the puncturing needle.

* * * * *